United States Patent [19]

Leuschner

[11] 4,375,466
[45] Mar. 1, 1983

[54] METHOD OF DETERMINING AND TREATING AFFECTIVE ILLNESS

[76] Inventor: Janet Leuschner, 4614 Fifth Ave., Apartment 407, Pittsburgh, Pa. 15213

[21] Appl. No.: 139,706

[22] Filed: Apr. 14, 1980

[51] Int. Cl.³ .................. A61K 47/00; A61K 31/135; G01N 33/48
[52] U.S. Cl. .......................................... 424/1; 424/9; 424/330; 436/57; 436/112; 436/111
[58] Field of Search ....................... 424/1, 1.5, 9, 330; 23/230 B

[56] References Cited

PUBLICATIONS

Meltzer et al., Arch Gen. Psychiatry, vol. 38, Dec. 1981, pp. 1322–1326.
Arora et al., Clinica Chimica Acta, vol. 118, 1981, pp. 225–233.
Rowe et al., Science, vol. 199, Jan. 27, 1978, p. 436.
Tuomisto et al., Nature, vol. 262, Aug. 12, 1976, pp. 596–598.
Tuomisto, J. Pharm. Pharmac., vol. 26, 1974, pp. 92–100.
Tuomisto et al., Chem. Abs., vol. 92, 1980, Ab No. 92:20181n.
Tuomisto et al., Chem. Abs., vol. 93, 1980, Ab No. 93:142524t.
Ehsanullah, Chem. Abs., vol. 93, 1980, Ab No. 93:37527y.
Born et al., Chem. Abs., vol. 93, 1980, Ab No. 93:887q.
Coppen et al., Chem. Abs., vol. 94, 1981, Ab No. 94:202768h.
Wirz–Justice, J. Neural Transmission, vol. 42, 1978, pp. 45–53, 55–62.
Wirz–Justice, Chem. Abs,, vol. 88, 1978, Ab Nos. 88:187613, 88:187614.
Coppen, Clin. Chim. Acta, vol. 87, 1978, pp. 165–168.

*Primary Examiner*—Anna P. Fagelson
*Attorney, Agent, or Firm*—Webb, Burden, Robinson & Webb

[57] ABSTRACT

A method of determining affective illness (i.e. mood disorders) involves serological testing. The serotonin uptake of the patient's blood platelets is determined and compared with a standard blood platelet serotonin uptake characteristic of a particular type of affective illness to determine the patient's type of affective illness. A method of treating a patient having a particular affective illness is provided which includes treating the patient with an effective amount of at least one drug which is effective in treating persons having the same blood platelet serotonin uptake as the patient.

5 Claims, 1 Drawing Figure

METHOD OF DETERMINING AND TREATING AFFECTIVE ILLNESS

BACKGROUND OF THE INVENTION

This invention relates to the determination and treatment of affective illness.

DESCRIPTION OF THE PRIOR ART

"Affective illness" as used herein means and refers to mood disorders of recurrent depression and/or mania where patients are characterized as depressive or manic-depressive. A manic-depressive is a person who experiences intervals of depression, normalcy and hypomania or mania. A depressive is a person who experiences intervals of depression and normalcy. Manic-depressives are also characterized as bipolars and depressives as unipolars. Generally, the type of drugs used in treating bipolar and unipolar disorders substantially differ, and the drug which is effective in treating bipolar disorder is not necessarily effective in treating unipolar disorder.

When an affectively ill patient is first voluntarily admitted to a psychiatric hospital or first seeks psychiatric or psychological treatment, he is normally in a depressed condition. This is because persons who are experiencing normal moods and those experiencing hypomania are quite satisfied with their psychological state. Thus, the most prevalent symptom when first examined, i.e. general behavior, is characteristic of both bipolar and unipolar disorders. The treating physician must accurately determine from which type of mood disorder the patient is suffering in order to prescribe the appropriate drug to alleviate the psychiatric condition, i.e. depression.

Typically, a series of psychological tests are performed upon the patient which are a series of questions and answers and may include the response to certain stimuli which aid in determining whether a patient is unipolar or bipolar. Typical tests are the RDC (Research Diagnostic Criteria) and the SADS. Once having performed these psychological tests the physician selects the appropriate drug, depending on whether the patient is diagnosed as unipolar or bipolar. If the external manifestations of the patient during the testing process indicate that the patient is bipolar when, in fact, the patient is unipolar, the prescribed drug will not be effective in alleviating the symptoms and vice versa. For example, it has been found that tranylcypromine in the sulfate form (2-tranylcypromine sulfate) and other monoamine oxidase inhibitors are helpful in alleviating the depression in bipolar patients, whereas the same drug type is undesirable and may be ineffective or harmful in treating unipolar patients. In unipolar patients it has been found that amitriptyline in the hydrochloride form (10,11-dihydro-N,N-dimethyl-5H-dibenzo [a,a]-cycloheptene-$\Delta^{5y}$-propylamine hydrochloride) and other tricyclopropylamine derivatives, including dibenzocycloheptadine derivatives, are useful in alleviating depression.

It has been recognized that the serotonin (5-hydroxytryptamine) in the cells of the brain stem has an affect upon the mood of the patient. Thus, the administration of monoamine oxidases has been hypothesized to increase the concentration of serotonin in storage sites throughout the nervous system. In "Uptake and release of $^{14}$C-5-hydroxytryptamine by platelets in affective illness" by Shaw et al. published in *J. Neurol. Neurosurg. Psychiat.*, 1971, Vol. 34, pp. 224–225, the authors came to the conclusion that serotonin uptake or binding mechanisms have little to do with affective illness.

In accordance with the present invention, it has been discovered that serotonin uptake in blood platelets of patients is characteristic of a particular mood disorder and, further, that there is a correlation between serotonin uptake of the patient's blood platelets and the particular drug which should be administered to alleviate the symptoms of the particular mood disorder.

BRIEF DESCRIPTION OF THE INVENTION

A method of determining mood disorders involves serological testing of the patient. The serotonin uptake of the patient's blood platelets is determined and compared with the standard blood platelet serotonin uptake characteristic of a particular type of mood disorder to determine the type of mood disorder of the patient. In addition, a method of treating a patient having a mood disorder is provided, which includes treating the patient with an effective amount of at least one drug which is effective in treating persons having the same range of blood platelet serotonin uptake as the patient.

DETAILED DESCRIPTION OF THE INVENTION

Figure 1:
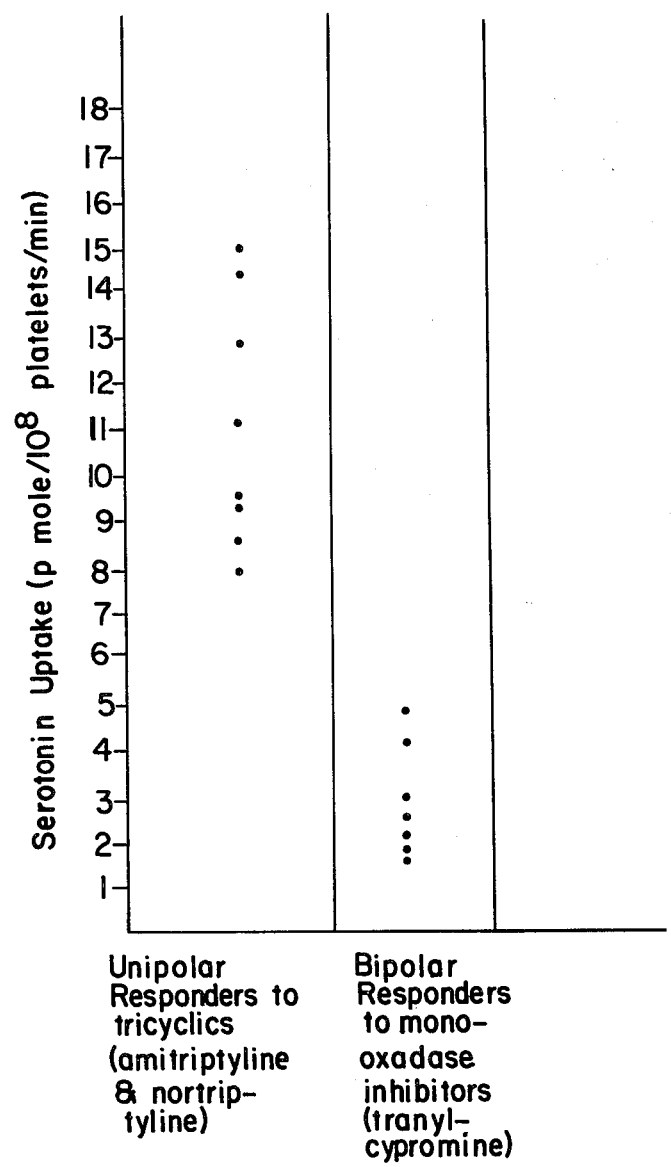
FIG. 1 is a table showing the results of a series of tests in which patients were treated for blood platelet serotonin uptake.

The determination of serotonin uptake of the patient's blood platelets as indicative of various mood disorders was determined in the following manner. Primarily affectively ill persons were judged to be from moderately to severely ill as measured by the Beck, Hamilton or PPRS Global tests, and either unipolar or bipolar by the SADS and RDC psychological tests. Any person having a medical or neurological problem was excluded for the purposes of determining serotonin uptake of the affectively ill persons. Those persons who established the standard serotonin uptake characteristic of specific affective illness were monitored as drug free for two to four weeks prior to testing for serotonin uptake. During the two week to four week drug-free period, these persons were given a placebo trial, and any who responded to these placebo trials were withdrawn.

Fifteen milliliters of blood were drawn from patients with a plastic syringe and stainless steel gauge 20 needle. All test tubes and pipettes were also plastic to prevent interference of glass with the test. Immediately after venepuncture, the blood sample was gently mixed with 1.5 milliliters of anticoagulant (27 millimolar disodium ethylenediaminetetraacetic acid, 120 millimolar sodium chloride, and 6 millimolar glucose). The whole blood was centrifuged at 350×g at room temperature for fifteen minutes; the platelet rich plasma was then pipetted off. The platelet rich plasma was mixed gently again to assure uniformity of various platelet populations within the plasma and the plasma was pipetted into aliquots of 0.5 milliliter each. Three milliliters of 0.11 molar potassium phosphate buffer adjusted to pH 7.35 with 10 normal aqueous NaOH were added to each aliquot to insure stabilization of pH. Half the aliquots were preincubated at 37° C. in a shaking water bath for ten minutes and the other half in an ice water bath (4° C.) for ten minutes. 0.5 milliliter of 0.9 percent (w/v)

saline containing $10^{-6}$ molar $^{14}C$ labeled 5-hydroxytryptamine-creatinine sulfate was then added to each sample's respective water bath. The uptake reaction was stopped by adding 1.0 milliliter of ice-cold 3 percent (w/v) formaldehyde in 0.9 percent (w/v) saline to each sample; all samples were then placed in the ice water bath to insure a 4° C. temperature.

To isolate the platelets, the samples were centrifuged at $2500 \times g$ at 0° C. for fifteen minutes. The test tubes were then inverted, given two minutes to thoroughly drip and then dried with a rolled paper towel to about an inch from the test tube bottom.

The remaining platelet pellet was solubilized in 0.5 milliliter of Soluene (dimethyl undecyl dodecyl quaternary ammonium hydroxide) and placed in a shaking water bath overnight. The sample was then prepared for radiospectroscopy by adding 5 milliliters of Econofluor scintillation fluid to each sample and the samples were poured into scintillation vials. Samples were counted for twenty minutes each in a Packard Tri-Carb Model 3390 Liquid Scintillation spectrometer.

The values of the 4° C. incubated sample were subtracted from the 37° C. sample so as to consider only the serotonin that entered each platelet, not that clinging to the platelet outer surface or the test tube. The resultant uptake was then expressed in picomoles of 5-hydroxytryptamine/$10^8$ platelets/minute. A platelet count was done from a sample of the original undiluted platelet rich plasma.

A series of patients were treated for blood platelet serotonin uptake as previously described. FIG. 1 shows the results of the testing. Thus, as can be seen from FIG. 1, those patients having blood platelet serotonin uptake of generally less than six picomoles/$10^8$ platelets/minute responded to tranylcypromine sulfate and, additionally, were diagnosed as manic-depressive or bipolar. Those patients who responded to amitriptyline had serotonin uptakes of generally six or greater picomoles/$10^8$ platelets/minute. These responders to amitriptyline were diagnosed as depressives. In addition to response to monoamine oxidase inhibitors, those patients with serotonin uptakes of less than five, when treated with lithium, were responsive thereto as inducing a return to normalcy.

In many instances, persons who are diagnosed according to psychological tests for affective illness are misdiagnosed and misprescribed because the external manifestations of the particular affective illness are sometimes deceiving. However, in accordance with the present invention, the determination of the particular affective illness is done by a serological test and, more importantly the serological test provides a means for selecting a drug to which the particular patient responds.

One particular problem in the diagnosis and treatment of affective illness is that a patient may exhibit behavior which is characteristic of a unipolar disorder when, in fact, that patient will only respond to medications effective in treating bipolars. Thus, as used herein "bipolar" and "unipolar" refer to the biochemical condition rather than an absolute behavioral condition. In accordance with the present invention, patients who exhibit unipolar behavior and are biochemical bipolars will have blood platelet serotonin uptake concomitant with other patients who are both behavioral and biochemical bipolars and these patients can be treated accordingly.

In another aspect of the invention, the serotonin assay method previously set forth differs with respect to the prior art in that: (1) a higher concentration of serotonin was used and (2) about 23 percent of the extra cellular fluid was the added potassium phosphate buffer. The assay in accordance with the present invention utilizes about ten times the amount of $^{14}C$-5-hydroxytryptamine to the same amount of platelet rich plasma over the prior art. This additional serotonin aids in spreading the unipolar and bipolar groups apart by enlarging the overall serotonin uptake, and also emphasizes the seemingly decreased role of passive diffusion played in serotonin uptake in bipolar patients. The greater the concentration of serotonin in the assay, the greater the difference between the bipolar and unipolar is demonstrated. As a result, in patients who yielded more platelet rich plasma than needed for the assay itself, the assay was repeated utilizing the potassium buffer adjusted to pH 6.1 and added about one-fifteenth as much serotonin as the original assay so as to observe the active uptake with little or no passive diffusion. The results were a significant difference between the groups. In accordance with the assay procedure previously described, 0.3 milliliter of 0.11 molar potassium phosphate buffer was added to the 0.5 milliliter of serotonin solution ($10^{-6}$) and 0.5 milliliter of platelet rich plasma. Therefore, a significant portion, 23 percent, of the extra cellular fluid was this added buffer, which thereby increased the extra cellular potassium concentration.

Thus, in accordance with the present invention, a method of assaying serotonin uptake in the blood platelets of patients is provided. Accordingly, after the serological test is conducted on a particular patient, the patient can be diagnosed as bipolar or unipolar or otherwise diagnosed with a particular affective illness and be treated with the particular drug to which he will respond.

Although the invention has been described with reference to specific materials and specific methods, the invention is only to be limited so far as is set forth in the accompanying claims.

I claim:

1. A method of treating a patient having an affective illness with an effective drug comprising:
    obtaining a serological sample from the patient;
    measuring the serotonin uptake of the blood platelets in the sample; comparing the measured blood platelet serotonin uptake of the patient with a standard blood platelet serotonin uptake characteristic of persons having a particular type of affective illness to determine the type of affective illness of the patient; and
    treating the patient with an effective amount of at least one drug which is effective in treating affectively ill persons having the same range of blood platelet serotonin uptake as the patient.

2. The method of claim 1 wherein the serotonin uptake of the blood platelets is measured by:
    mixing a serological sample of the patient with an anticoagulant;
    separating platelet rich plasma from the serological sample;
    adding a predetermined amount of radioactive serotonin to the platelet rich plasma;
    isolating the platelets having taken up the radioactive serotonin; and
    measuring the radioactivity of the platelets to determine the serotonin uptake.

3. The method of claim 1 wherein said drug is selected from the group consisting of monoamine oxidase inhibitors and tricyclic amines.

4. The method of claim 3 wherein said monoamine oxidase inhibitor is tranylcypromine.

5. The method of claim 3 wherein said tricyclic amine is selected from the group consisting of amitriptyline and nortriptyline.

* * * * *